United States Patent

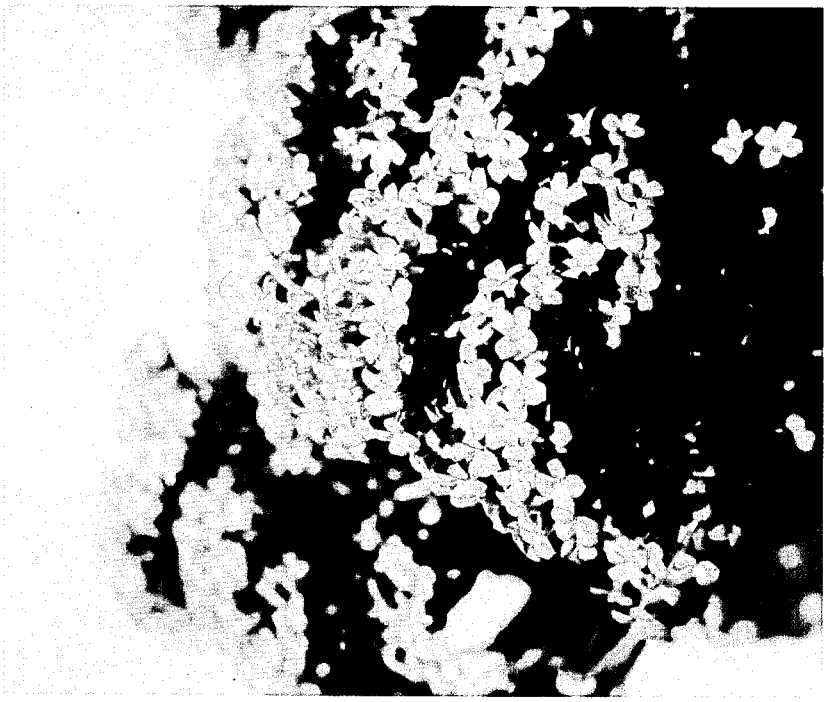
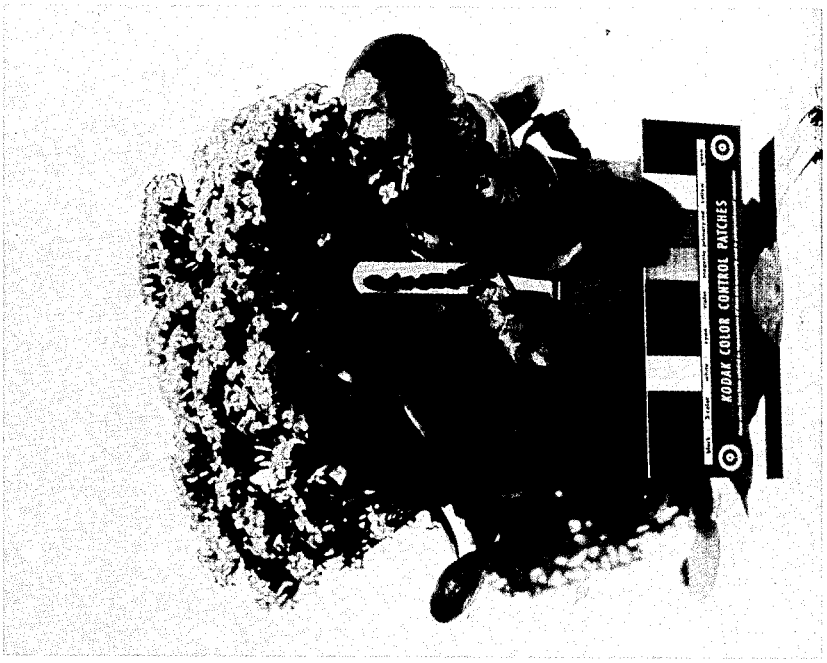
KODAK COLOR CONTROL PATCHES

Plant Pat. 3,821

Patented Dec. 23, 1975

1

3,821

KALANCHOE PLANT

Roy N. Pittman, Amarillo, Tex., assignor to J and L Plants, Incorporated, Canyon, Tex.

Filed May 13, 1974, Ser. No. 469,700

Int. Cl. A01h 5/00

U.S. Cl. Plt.—68 1 Claim

The present invention relates to a new and distinct variety of kalanchoe plant which was originated by me by crossing the kalanchoe variety known as "Gold Dust" (unpatented) with an unnamed and unpatented kalanchoe variety, the former being the seed parent and the latter being the pollen parent.

As the result of this breeding, I have produced a new and improved kalanchoe variety which is distinguished from its parents, as well as from all other varieties, as evidenced by the following unique combination of principal characteristics which are outstanding in the new variety:

(1) A short, self-branching, upright and compact habit of growth;
(2) Attractive, flexible foliage of medium size and Fern Green color;
(3) An early blooming habit, ranging from about 7 to 10 days earlier than its pollen parent, as well as earlier than most other hybrid varieties;
(4) The profusion of its blooms which are borne on short, sturdy flower stems above the foliage;
(5) A distinctive and attractive cinnamon flower color when flowers first open, becoming lighter and more golden, between apricot and burnt orange as the flowers mature;
(6) A pleasant and distinctive lemon fragrance of the flowers;
(7) An adaptability to photoperiod manipulation for year around flowering; and
(8) Especial suitability for potted plant use.

Asexual reproduction of my new kalanchoe variety by cuttings, as performed by me in greenhouses located at Canyon, Tex., shows that the foregoing characteristics and distinctions come true and are established and transmitted through succeeding propagations.

The accompanying drawing shows a typical blooming plant and a close-up view of the flowers of my new variety as depicted in color as nearly true as it is reasonably possible to make the same in a color illustration of this character.

The following is a detailed description of my new kalanchoe variety, with color terminology in accordance with the Exotica Horticultural Color Guide, published by Roehrs Company, except where general color terms of ordinary dictionary significance are obvious:

PARENTAGE: Seedling.
- Seed parent—"Gold Dust."
- Pollen parent—An unnamed tall, yellow, scented kalanchoe variety of unknown origin.

PROPAGATION: Holds its distinguishing characteristics through succeeding propagations by direct rooting of cuttings.

LOCALITY WHERE GROWN AND OBSERVED: Canyon, Tex.

PLANT:
- Form—Much-branched; upright, compact.
- Growth habit—Medium vigor; upright; self-branching; compact; short (from about 10 inches to 12 inches tall).
- Rooting habit—Roots easily from any part of stem and forms a fibrous root system.
- Blooming habit—Flowering occurs naturally about December 1st.
- Blooming season—Adaptable to year around flowering by day length manipulation.

FOLIAGE:
- Size—Medium; average length when mature about 3 inches; average width about 2⅜ inches.
- Quantity—Normal.
- Color—New foliage—Upper side—Fern Green, No. 83. Under side—Fern Green, No. 83−. Old foliage—Upper side—Fern Green, No. 83+. Under side—Fern Green, No. 83−.
- Shape—Basically oblong, with obtuse tip and truncate base.
- Texture—Upper side—Glossy; smooth. Under side—Smooth.
- Margin—Crenate.

DISEASE RESISTANCE: Much more resistant to common kalanchoe diseases than old standard varieties, as determined by comparison with other varieties grown under the same greenhouse conditions at Canyon, Tex.

FLOWERS: Complete.
- Size—Diameter—About ½ inch. Depth—About 9/16 inch. Petals—Length—About 3/16 inch. Width—About 5/32 inch.
- Form—Compound umbel; section petals united; ovary superior.
- Color—Upper side—Near Cinnamon, No. 13 when flowers first open, becoming lighter and more golden, between Apricot, No. 11 and Burnt Orange, No. 12 as the flowers mature. Under side—Chrome Yellow, No. 10, with throat of corolla Buttercup Yellow, No. 4.
- Blooming period—From about 4 to 5 weeks.

FRUIT: None.

HARDINESS: Good in range from 55° F. to 100° F.

GENERAL OBSERVATIONS: Has all the qualities for good potted plants, with short, upright and compact growth, distinctive and attractive flowers of cinnamon color, and a unique lemon flower fragrance.

I claim:

1. A new and distinct variety of kalanchoe plant, substantially as herein shown and described, characterized particularly as to novelty by the unique combination of a short, self-branching, upright and compact habit of growth, attractive, flexible foliage of medium size and Fern Green color; an early blooming habit, ranging from about 7 to 10 days earlier than its pollen parent, as well as earlier than most other hybrid varieties; the profusion of its blooms which are borne on short, sturdy flower stems above the foliage; a distinctive and attractive cinnamon flower color when the flowers first open, becoming lighter and more golden, between apricot and burnt orange as the flowers mature; a pleasant and distinctive lemon fragrance of the flowers; an adaptability to photoperiod manipulation for year around flowering; and especial suitability for potted plant use.

No references cited.

ROBERT E. BAGWILL, Primary Examiner